United States Patent [19]

Ringle

[11] Patent Number: 5,094,255

[45] Date of Patent: Mar. 10, 1992

[54] ACRYLIC DENTAL FLOSS AND METHOD FOR MANUFACTURE

[76] Inventor: Larry L. Ringle, 645-2 Woodside Sierra, Sacramento, Calif. 95825

[21] Appl. No.: 307,634

[22] Filed: Feb. 8, 1989

[51] Int. Cl.⁵ .............................................. A61C 15/00
[52] U.S. Cl. .................................. 132/321; 132/329; 57/295
[58] Field of Search ............... 132/321, 322, 323, 324, 132/325, 326, 327, 328, 329; 57/295

[56] References Cited

U.S. PATENT DOCUMENTS

| | | | |
|---|---|---|---|
| 2,612,177 | 9/1952 | Footer | 132/324 |
| 2,931,371 | 4/1960 | Petitta | 132/324 |
| 3,837,351 | 9/1974 | Thornton | 132/321 |
| 3,838,702 | 10/1974 | Standish et al. | 132/321 |
| 3,930,059 | 12/1975 | Wells | 132/321 |
| 4,011,658 | 3/1977 | Tarrson et al. | 132/329 |
| 4,029,113 | 6/1977 | Guyton | 132/321 |
| 4,080,777 | 3/1978 | Griset, Jr. | 57/208 |
| 4,155,216 | 5/1979 | Griset, Jr. | 57/295 |
| 4,159,619 | 7/1979 | Griset, Jr. | 57/295 |
| 4,184,316 | 1/1980 | Griset, Jr. | 57/295 |
| 4,215,478 | 8/1980 | Thomas et al. | 132/323 |
| 4,265,258 | 5/1981 | Eaton II | 132/321 |
| 4,523,600 | 6/1985 | Donovan | 132/321 |
| 4,583,564 | 4/1986 | Finkelstein et al. | 132/321 |
| 4,832,063 | 5/1989 | Smole | 132/321 |

*Primary Examiner*—Gene Mancene
*Assistant Examiner*—Frank A. LaViola
*Attorney, Agent, or Firm*—Bernhard Kreten

[57] ABSTRACT

Dental floss formed from acrylic fiber having a leader integrally connected with the fiber allowing the fiber to be placed between gaps of teeth and a gum line.

18 Claims, 2 Drawing Sheets

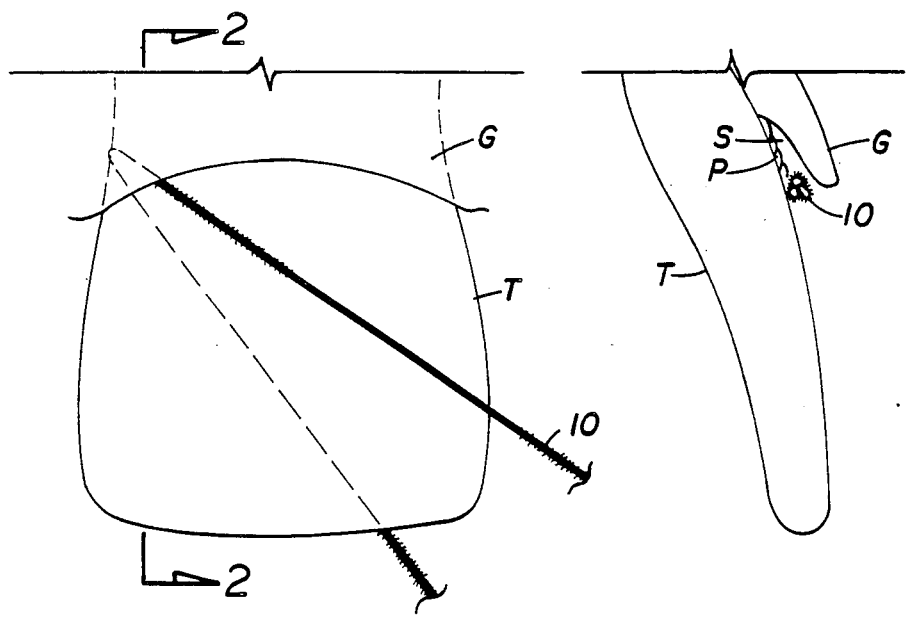
FIG. 1
FIG. 2
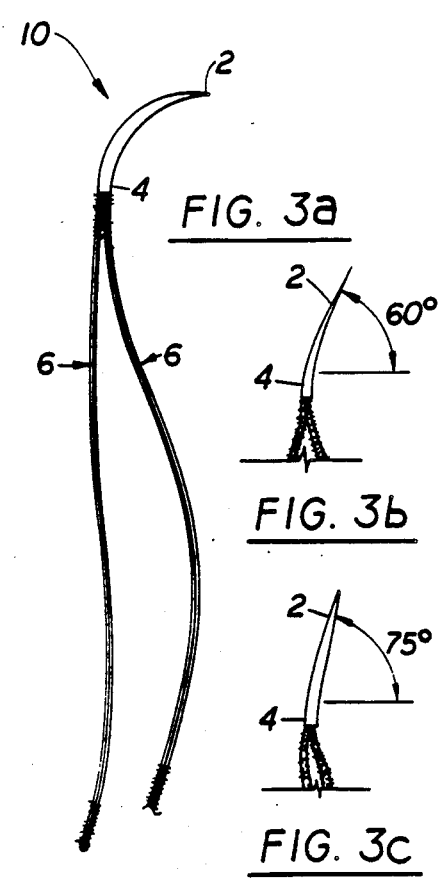
FIG. 3a
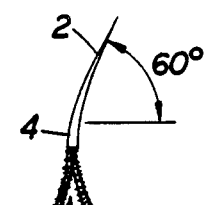
FIG. 3b
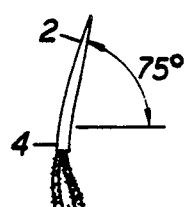
FIG. 3c
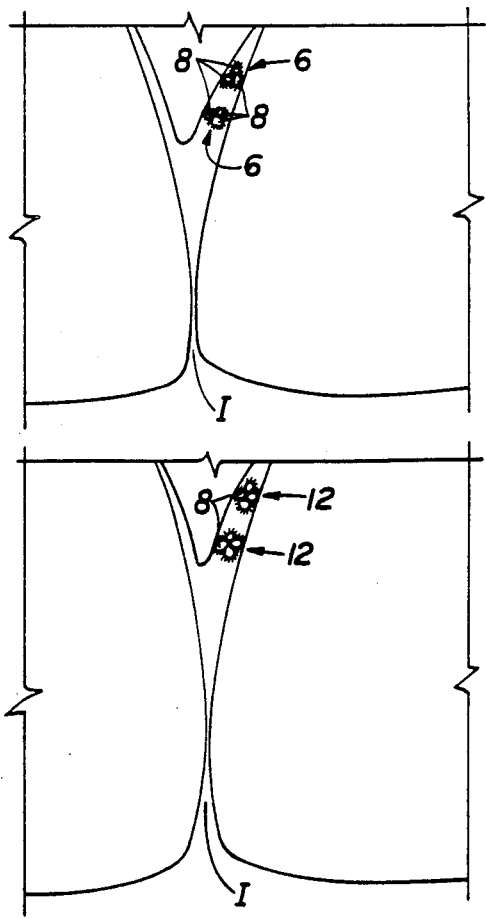
FIG. 4a
FIG. 4b

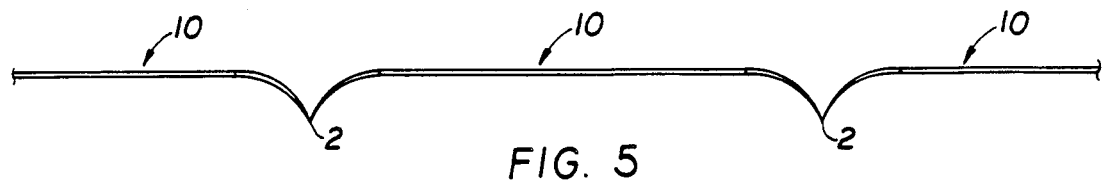
FIG. 5
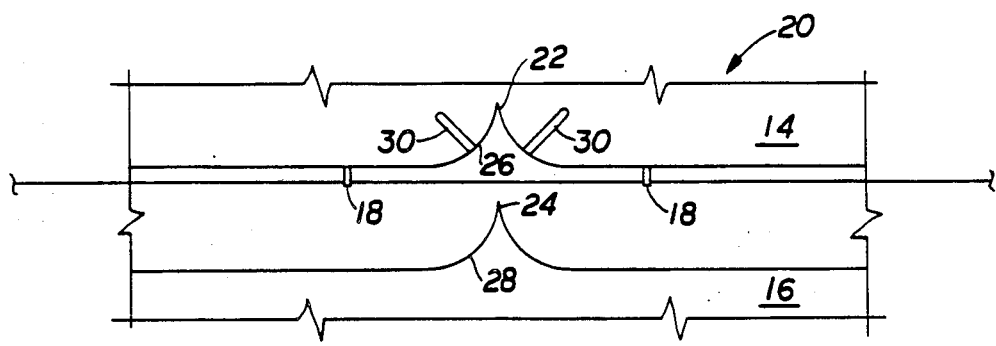
FIG. 6
FIG. 7
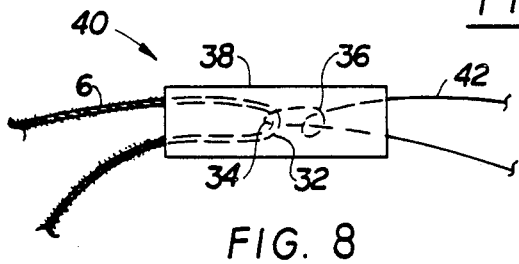
FIG. 8
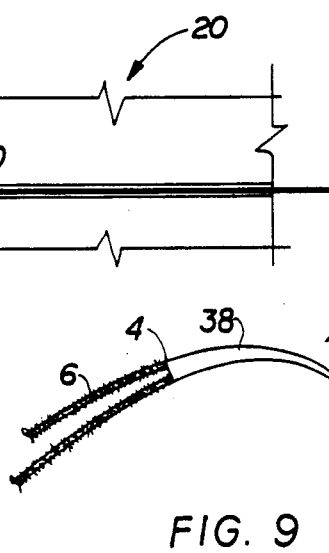
FIG. 9
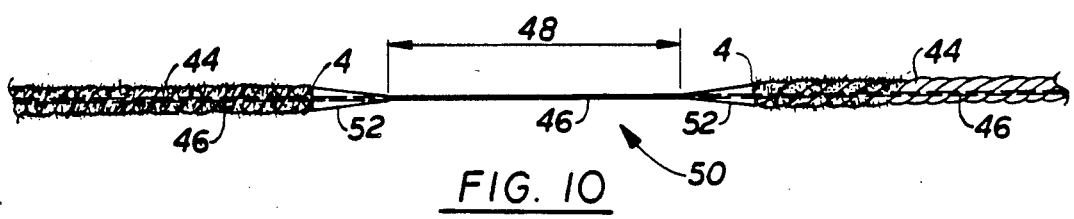
FIG. 10
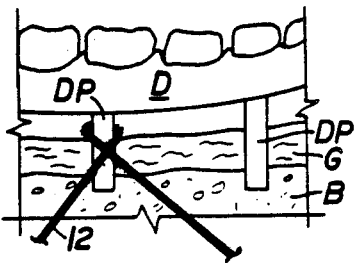
FIG. 11
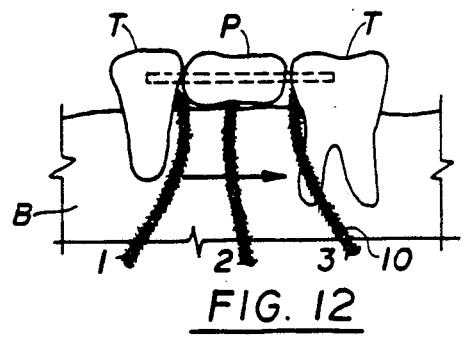
FIG. 12

ACRYLIC DENTAL FLOSS AND METHOD FOR MANUFACTURE

FIELD OF THE INVENTION

The following invention relates generally to an improved form of dental floss having exceptional plaque-removing capabilities and a method for manufacturing same. More particularly, the invention relates to multiply acrylic fiber which has an excellent ability to remove plaque. A leader is formed on at least one free end of the acrylic fiber to facilitate placement of the floss in plaque-collecting areas.

BACKGROUND OF THE INVENTION

Since the mid-1960's plaque has been identified as playing at least a major role in causing dental problems both with respect to caries and periodontal disease. However, the actual mechanism by which plaque operates is still subject to conjecture. Plaque, a film of mucus which is produced in the mouth, is a known medium which can harbor bacteria both on the tooth and adjacent gum tissue. It is generally recognized that removal of plaque is essential for promulgating oral hygiene.

Although substantial research and product engineering has occurred over the last 20 years with a view towards effectively removing plaque, certain difficulties still exist. The following prior art describes the ongoing efforts of others attempting to solve this long-standing problem which has yet evaded solution, and these prior art citations are included to discharge applicant's acknowledged duty to disclose prior art with which he is familiar:

U.S. Pat. No. 4,265,258, Eaton, May 5, 1981
U.S. Pat. No. 4,070,815, Negishi, et al., Jan. 31, 1978
U.S. Pat. No. 4,523,600, Donovan, June 18, 1985
U.S. Pat. No. 2,381,142, Stonehill, Aug. 7, 1945
U.S. Pat. No. 3,896,824, Thornton, July 29, 1975

Generally, the techniques for plaque removal are predicated on two principles. The first involves plaque removal through "washing" the plaque from the mouth area by means of liquids. Second, plaque removal has been attempted by mechanical brushing.

With respect to washing, certain mouthwashes are commercially marketed without prescription which purport to be effective in plaque control. These however are not registered with the Food and Drug Administration, and are merely listed as cosmetics. Available research data suggests that these mouthwashes are less than completely effective. A second known liquid, Peridex, is available under prescription and is a known plaque-removing liquid, but is objectionable to the extent that side effects are exhibited in some individuals. These side effect include adverse teeth staining and affecting one's taste perception. Even with an effective liquid, the film-like quality of plaque thwarts highly efficient removal through mere mouthwashing, and is singularly ineffective when tryng to remove plaque in the sulcus area of one's mouth, i.e., the narrow trough-like gap between one's tooth and the gum tissue. This is also critical interproximally (in between the teeth) since this is where most periodontal disease and caries occur.

To a certain extent, plaque formation is not a problem on tooth surfaces that can receive direct mechanical contact with an instrument such as a brush which effectively breaks up the plaque film and therefore allows the plaque and its associated entrained bacteria to be carried away. Many brush manufacturers claim their bristles will go below the gum (in the sulcus) on the buccal and lingual—not interproximally, however, thus, along those areas where direct brush contact is possible, plaque buildup is less of a problem. However, brushes still are quite ineffective in removing plaque both along the area immediately below the gum line, i.e., the sulcus and interproximally.

As knowledge with respect to the role that plaque plays in dental disease has grown, so too has the change in the design of various types of dental floss. While dental floss was once used substantially as a toothpick for the removal of entrained matter caught between teeth, various changes in dental floss appearance, praticularly in the last few years reflect the belief that dental floss can be used to remove plaque in areas normally inaccessible by any other means particularly when used daily. Most designs involve contouring the external configuration of nylon or polyethylene to form an abrasive surface which can break up the plaque film under the gum line and between teeth to solve the problem. Earlier attempts have included the use of fibers formed from silk, cotton, nylon or blends thereof.

All of these known prior art flossing structures are less than desirable in that they are either too abrasive which adversely effects the enamel on the tooth, are too sharp which can cause damage to the gum tissue by cutting the gums, or are ineffective in removing the plaque. Moreover, taking this floss under the gum actually causes pain and the patient, therefore, will not take floss under the gum to remove plaque in the normal 3 mm sulci.

SUMMARY OF THE INVENTION

The instant invention is distinguished over the known prior art in that the inventor has discovered that acrylic fiber advantageously removes unwanted plaque yet does so without damaging either the tooth's enamel or gum's tissue. While the exact reasons why acrylic fiber are superior to known prior art materials may be the basis of some speculation and conjecture, the inventor's extensive "split-mouth" studies, comparing the known prior art to acrylic fiber demonstrates efficacy.

One primary reason appears to be the densure or "fuzziness" of the acrylic fiber when it is configured as yarn. The yarn exhibits a plurality of outwardly extending free ends which appear well suited to reach within the bottom most area of the sulcus and gently remove plaque therefrom. It is to be noted that in a healthy mouth, the depth of the trough defining the sulcus is approximately 3 mm interproximally. Plaque is manufactured by the body and forms in this trough area. Since plaque consists of bacteria, "fresh" plaque (i.e., less than 24-36 hours) is not believed to be harmful this is because it does not contain a high number of pathogenic bacteria. When the plaque becomes old, however, the bacteria present will attack the tooth and tissue area against which it abuts, causing periodontal disease. Regular use of floss formed from acrylic fiber stops the infection.

A second advantage attributable to the use of acrylic fiber as a dental floss involves the coefficeint of friction associated with the acrylic fiber when it is configured as a yarn. Because the mechanical flossing motion is oscillatory, back and forth along the length of the floss strand, friction is generated and dissipated in the form of heat when using acrylic fiber as a floss. This provides a thermal sensor to the user of the floss as to the relative vigor with which the flossing should be conducted for best results. Unlike prior art fibers used in flossing which have coefficients of friction different from acrylic fiber, and therefore result in either too vigorous or too light a flossing motion, acrylic fiber's coefficient of friction appears to correlate with effective flossing technique.

A third possible reason for the enhanced benefits associated with acrylic fiber according to the instant invention devolves from gingival stimulation and not inflammation as can occur with some prior art devices. The cross-sectional diameter of the yarn formed from the acrylic fiber according to the present invention is kept within certain ranges depending upon the characteristics of the flosser's mouth. Factors include the relationship of one's gums to the teeth, the interproximal gap between adjacent teeth and the depth of pockets within the sulcus. For individuals who are not candidates for periodontal surgery and have relatively healthy teeth and tissue, one strand of four-ply or two strands of two-or three-ply acrylic fiber have been found to be an effective hygienic apparatus. For post-periodontal patients or those people with dental implants, a double-strand of at least four-ply acrylic fiber can provide the desired benefits.

A fourth known reason involves the beneficial characteristics of acrylic fiber as a flossing tool. The acrylic fiber appears to have the requisite absorbency to actually serve as a carrier in removing unwanted plaque. Thus, whereas the fibers initially served to break up the film placed on the teeth and gums of the flosser, the fibers also absorb the plaque and remove it from the site of potential harm. The yarn thus buffs the plaque off.

A fifth reason involves the disturbance of existing sites of necrosis and festering inflammation. When the floss is used regularly, objectionable odors associated with halitosis abate as a function of time.

Viewed in its essence, the instant invention is directed to dental floss formed from acrylic fiber. The floss may be formed from braiding a plurality of acrylic fiber strands, and in one form of the invention, sets of braided strands are disposed in stacked registry and used simultaneously to occupy as much of a gap as exists between adjacent teeth and underlying support tissue.

Because excessive clearance between the floss, the teeth and the tissue is not desired, the floss according the instant invention is best used with a leader. Because the leader works most efficiently when it is of relatively small dimension and is somewhat textured, it does not normally exhibit the same characteristics as the floss which is intended to contact and remove the plaque. Consequently, the leader is characterized in its relatively small cross-sectional diameter when compared with the floss and has a substantially lower coefficient of friction than the floss. Thus, the leader can pass between the interproximal gap or area of tangency between adjacent teeth. The floss itself is pulled between teeth below the interproximal area of tangency near the base of the exposed teeth, above the gum line and wrapped around the line angles (i.e., "corners" of a tooth).

The leader may be formed from modified acrylic fiber or from another material. When acrylic fiber itself is to be modified, portions of the fiber which are to serve as leaders are treated by one or more of the following: solvent, embedding plastic, heat, pressure or tension. As described infra, these techniques when approximately manipulated will alter the characteristic of the acrylic fiber at a designated leader portion thereby facilitating placement of the floss between teeth.

Other types of leaders which are not integrally formed with the acrylic fiber can also be used but then must be joined to the acrylic fiber and then contoured to provide a gradual transition between the leader and the floss portion. Various techniques for joining the leader to the floss including bonding, weaving, fusing and encapsulating will also be discussed infra.

The essential feature is to attach the leader in such a way that the floss can be used in relatively tight clearances with minimal dexterity requiements imposed upon the user. A hallmark of the instant invention is it's ability to be used within the mineral clearances indigenous with the flossing operation and by individuals having relatively modest dexterity skills to increase the likelihood that the user will not be dissuaded from practicing good oral hygiene techniques. It should be noted that any program of oral prophylaxis is predicated on habitual hygienic practices. One characteristic of the instant invention is that it closely emulates traditional flossing techniques to increase the likelihood that the device will be used on a regular basis with a minimal amount of disruption of pre-existing good dental habits.

OBJECTS OF THE INVENTION

Accordingly, it is a primary object of the present invention to provide a new and useful dental flossing implement.

A further object of the present invention is to provide not only a device as characterized above but also a preferred method for producing the instant apparatus.

A further object of the present invention is to provide a device as characterized above which is relatively inexpensive to manufacture, benefits from mass production techniques, and is durable and safe to use.

A further object of the present invention is to provide a device as characterized above which removes plaque from areas not accessible by known prior art instrumentalities.

A further object of the present invention is to provide a device as characterized above which has a co-efficient of friction such that the flosser has readily discernable feedback which correlates with the quantum of pressure for efficient use of the floss.

A further object of the present invention is to provide a device as characterized above which can be used as a presurgical prophylactic, a post-surgical prophylactic and with denture or bridge implants.

A further object of the present invention is to provide a device as characterized above which includes a plurality of fibrous free ends which can extend into the trough-like recess that exists between supporting tooth tissue and the teeth to not only remove plaque but also stimulate the gingiva.

Viewed from one vantage point, it is an object of the present invention to provide an instrumentality which is formed from an elongate strand of acrylic fiber material having a plurality of outwardly extending fibrous free ends which contact plaque and remove the plaque from the surface of a tooth and an adjacent sulcus between the tooth and its surrounding gum tissue.

Viewed from a second vantage point, it is an object of the present invention to provide dental floss formed from a strand of acrylic fiber having a cross-sectional diameter greater than interproximal spacing of adjacent teeth, and a leader extending from an end of the acrylic fiber strand having a cross-sectional diameter less than the interproximal tooth spacing.

Viewed from yet a third vantage point, it is an object of the present invention to provide a method for forming dental floss which includes treating an end of a strand of acrylic fiber to provide a cross-sectional diameter at the end of lesser dimension than a non-end portion of the fiber wherein the diameter is less than an interproximal tooth spacing of adjacent teeth to provide a leader for inserting the fiber between the teeth.

These and other objects will be made manifest when considering the following detailed specification when taken in conjunction with the appended drawing figures.

BRIEF DESCRIPTION OF THE DRAWING FIGURES

FIG. 1 is a front view of the apparatus according to the present invention in its intended environment.

FIG. 2 is a sectional view taken along lines 2—2 of FIG. 1 and shows fibrous ends absorbing and buffing off plaque.

FIG. 3 A-C is a plan view of the apparatus according to the present invention shown in FIG. 1.

FIG. 4A is a sectional view showing the floss as embodied by two strands of three-ply material which are vertically stacked.

FIG. 4B is similar to FIG. 4A but shows four-ply material. In pre-surgical situations this could be one strand of four-ply.

FIG. 5 shows the floss as it is embodied in a continuous strand, adapted to be stored on a spool or the like and dispensed in discrete segments.

FIG. 6 is a top plan view complemental to the floss shown in FIG. 5 embodying a mold in the open configuration to make the FIG. 5 floss.

FIG. 7 is a similar to FIG. 6 with the mold closed.

FIG. 8 shows a second embodiment according to the present invention being assembled.

FIG. 9 shows that which is shown in FIG. 8 in a finished, assembled configuration.

FIG. 10 reflects a third embodiment according the present invention.

FIG. 11 teaches the use of the instant invention in the embodiment of dental implants.

FIG. 12 shows the invention used under fixed bridges.

BRIEF DESCRIPTION OF THE PREFERRED EMBODIMENTS

Referring to the drawings now, wherein like reference numerals refer to like parts throughout the various drawing Figures, reference numerals 10, 40 and 50 are directed to the first, second and third embodiments respectively according to the present invention. Reference numeral 20 is directed to a mold which can advantageously mass produce the apparatus in one embodiment.

As shown in FIG. 1, which is a front view of a tooth having floss 10 disposed thereon, and in conjunction with FIG. 2, plaque P is removed by the motion of the floss along its longitudinal extent in an oscillatory pattern, wherein plaque is buffed off by its contact with the outwardly extending filaments and fiber associated with the acrylic 10. In essence, the area of transition between the tooth T and its area of protection by the gum G is the sulcus S within which plaque is formed and retained. As time passes, the plaque bacteria have a deleterious effect both on the teeth and the supporting gum and bone. By use of the apparatus shown with greater detail in FIG. 3, the plaque can be broken up, buffed off and carried away on the floss 10.

As shown in FIGS. 3 and 4, the floss 10 includes a pair of elongate strands 6 of acrylic fiber braided from a plurality of filaments 8. As shown in FIG. 4A, a three-filament configuration 6 can be used, but as FIG. 4B suggests, a four-filament braid 12 also has utility. It is believed that this braiding can have other configurations and is included as being illustrative of what has known utility. Thus, a fewer or a greater number of strands would also have efficacy in this environment, depending upon the cross-sectional diameter of each filament. Where the acrylic fiber is of known commercial origin, such as that which is manufactured by Du-Pont or Monsanto, the three-and four-filament versions appear to work best.

Each segment of the floss 10 includes either a single or the depicted double-strands 6, a leader 2 and an area of transition 4. In a preferred form of the invention, the leader 2 is formed with an arcuate shape as will be described with reference to FIGS. 5 through 7. The arcuate shape may form an included angle of 60°, 75° or perhaps even 90°, with respect to the strand 6.

When a continuous strand of discrete floss segments are desired as in FIG. 5, a mold 20 of FIG. 6 having an upper portion 14 and a lower portion 16 can be used to impart the curved configuration to the leader 2. Where the leader need not be curved, this mold section can be linear. In any event, either the mold upper and lower portions 14, 16 may include retention points 18 which grasp the acrylic fiber 6 in a fixed position. Where the leader is to be curved, a portion midway between the two retention points 18 includes a peak 22 on the upper mold 14 and a corresponding peak 24 on the lower mold 16, communicating to the retention points 18 respectively by upper curved wall 26 and lower curved wall 28. When the mold is closed, the retention points 18 grasp the acrylic fiber preventing advancement of the fiber and instead imparts a tensile loading on the acrylic fiber between the peak 22, 24 and the retention points 18. This causes a natural narrowing of the cross-sectional area of the acrylic fiber.

Sprues 30 allow communication within the interior of the mold cavity. The spruce allow either the admission of a solvent and/or a "potting" compound to be inserted within the mold cavity and impregnate the acrylic fiber. For example, where solvent is to be used, either ethylene carbonate or propylene carbonate is injected into the cavity through the sprue 30 to change the acrylic fiber back into its pre-processed configuration (polyacryl nitrile). When combined with suitable heat and pressure, only a fine misting of solvent is required, and the heat is actually used to dry the solvent off once the composition has re-stabilized. The leader is thus formed having a tapering smooth outer contour which expands downstream, as it approaches the untreated strands 6 at the area of transition 4.

Alternatively, rather than altering the characteristic of the acrylic fiber with a solvent, it is also possible to alter the configuration of the acrylic fiber by injection of the polyacryl nitrile through the sprues which would then instead serves as a potting compound which encapsulates the fibrous portion and forms the leader 2. Another alternative potting compound would be linear polyethylene which is injectd into the mold cavity through the sprues 30.

Typically, either the solvent or the potting process occurs in an environment which is beneficially affected by heat and pressure. Because there is a relationship between the selected heat and associated pressure utilized, the temperature in the mold cavity can range from 100–475° F. and the pressure can vary from 10 to 200 pounds per square inch. The two above-described precesses may also be enhanced in the presence of ultrasonic radiation. Typically, the frequency associated with the leader forming processing has an acceptable range of 25,000 to 75,000 cycles per second.

One specific example includes tensioning the acrylic, applying solvent, heating to 200 degrees F, physically tapering the leader as through a mandrel for approximately five munutes and then cooling the leader for five minutes.

With respect to FIG. 8, a second embodiment 40 is shown. In general the acrylic fiber is oriented to define a substantially U-shaped end 32. A segment of nylon floss 42 is similarly configured in a U-shape 34 such that the bight portion of each U-shaped segment overlaps. Optionally, the nylon floss can be retained on the acrylic fiber by means of a knot 36, for example a half-hitch knot. Thereafter, a heat shrink sleeve 38 is placed over the juncture between the acrylic fiber and floss, and heat is applied. The heat shrink, formed from a known family of materials such as polyolefin will constrict upon the transition 4 between the leader, now formed from nylon floss 42 and the main body portion 6 of the flossing device 40. FIG. 9 shows the trimmed, assembled configuration of FIG. 8.

FIG. 10 reflects a third embodiment 50 in which multistrand acrylic fiber 44 has a central core formed from leader material such as nylon 46. The leader itself is formed by providing a stripped-away area 48 exposing just the leader 46, and a conically tapering shroud 52 is placed at each transition 4 where the leader communicates with the multistrand acrylic fiber 44.

With respecdt to FIG. 11, the device according to the present invention used in conjunction with dental implants is illustrated. More particularly, conventional dental implants include a denture post DP supported from a bone B and extending up through the gum G of the dental patient. The denture post DP supports a denture D or fixed bridge spaced a distance from the gum line. As shown, any of the dental floss described here and above, but more particularly one having a curved leader can be used to circumscribe the dental post DP to prevent the entrainment of food thereat and to provide a buffing operation for removing plaque.

FIG. 12 reflects a use for the instant invention with fixed bridges. Bone B supports both natural teeth T. An interposed artificial tooth, i.e., a pontic P, is supported by teeth T such that clearance exists between teeth, P,T and bone B for floss 10,40 or 50.

Moreover, having thus described the invention, it should be apparent that numerous structural modifications and adaptations may be resorted to without departing from the scope and fair meaning of the instant application as set forth here and above and as defined here and below by the claims. For example, while the foregoing discussion was predicated on an assumption that acrylic fiber was the sole fiber used in forming the floss, it should be apparent that this fiber may be present in a lesser proportion so long as its characteristics of outwardly extending loose fibrous free ends, its coefficient of friction and ability to absorb and remove plaque, etc., be present in sufficient proportion to provide its effectiveness.

We claim:

1. Dental floss consisting of an elongate uninterrupted strand of acrylic fiber material having substantially uniform cross-sectional area along its length, said fiber having a plurality of outwardly extending fibrous free ends which contact plaque and remove the plaque from a surface of a tooth and an adjacent sulcus between the tooth and a gum tissue circumscribing the tooth, and leader means at one end of said acrylic fiber for inserting said acrylic fiber material into an interproximal space between one tooth and an adjacent tooth.

2. The floss of claim 1 wherein said leader means is integrally formed with said elongate strand, and an area of transition is provided between said leader means and said floss, said leader means tapering in a smooth contour from said area of transition.

3. The floss of claim 2 wherein said leader means has a generally arcuate configuration.

4. The floss of claim 3 wherein said leader means is impregnated with a potting compound which has a smooth external contour tapering to a point remote from said floss.

5. The floss of claim 2 wherein said area of transition between said floss and said leader means includes a U-shaped floss end draped over a corresponding U-shaped leader end which is tied in a knot, firmly affixing the two together.

6. The floss of claim 5 wherein said knot underlies a tapering heat shrink which provides a smooth transition from said leader to said floss.

7. Dental floss consisting of an elongate, uninterrupted strand of acrylic fiber having a substantially constant cross-sectional diameter along the length of said stand greater than interproximal spacing of adjacent teeth, and
   a leader means connecting with and extending from an end of said acrylic fiber strand said leader means having a cross-sectional diameter less than the interproximal tooth spacing.

8. The floss of claim 7 wherein said leader means is integrally formed with said strand, and an area of transition is provided between said leader and said floss which tapers in a smooth contour.

9. The floss of claim 8 wherein said leader has a generally arcuate configuration.

10. The floss of claim 9 wherein said leader is impregnated with a potting compound which has a smooth external contour tapering to a point remote from said floss.

11. The floss of claim 9 wherein the area of transition between said floss and said leader includes a U-shaped floss end draped over a corresponding U-shaped leader end which is tied in a knot, firmly affixing the two together.

12. The flqss of claim 11 wherein said knot underlies a tapering heat shrink which provides a smooth transition from said leader to said floss.

13. A method for forming dental floss including: treating an end of an elongate uninterrupted strand of acrylic fiber having a cross-sectional diameter greater than conventional interproximal tooth spacing, said end conditioned to provide a cross-sectional diameter at said end of lesser dimension than an intermediate non-end portion of the fiber by attaching a leader means thereto wherein the diameter of the leader is less than an interproximal tooth spacing of adjacent teeth to provide the leader means for inserting the fiber between the teeth.

14. The method of claim 13 wherein the end is treated by retaining a portion of the floss at two points, placing an area between the two points under tension, and altering a plurality of characteristics of the acrylic fiber between the retention points.

15. The method of claim 14 wherein the fiber is altered by applying a solvent, heat and pressure between the retention points.

16. The method of claim 14 wherein the treating includes encapsulating the area between the retention points in a potting compound.

17. A method for forming dental floss, including: treating an end of a stand of acrylic fiber to provide a cross-sectional diameter at the end of lesser dimension than a non-end portion of the fiber by attaching a leader means thereto wherein the diameter is less than an interproximal tooth spacing of adjacent teeth to provide a leader for inserting the fiber between the teeth, wherein said end is treated by retaining a portion of the floss at two points, placing the area between said two points under tension, and altering the characteristics of said acrylic fiber between the retention points, wherein said fiber is altered by applying a solvent, heat and pressure between said retention points, wherein said fiber between said retention points is distorted by pressing said fiber in a direction transverse to a longitudinal axis of said fiber and supporting it in an arcuate configuration in a mold cavity.

18. A method for forming dental floss, including: treating an end of a stand of acrylic fiber to provide a cross-sectional diameter at the end of lesser dimension than a non-end portion of the fiber by attaching a leader means thereto wherein the diameter is less than an interproximal tooth spacing of adjacent teeth to provide a leader for inserting the fiber between the teeth, wherein said end is treated by hooking a leader to a U-shaped portion of said fiber and encapsulating a juncture in heat shrink plastic.

* * * * *